United States Patent
Singh et al.

(10) Patent No.: US 12,343,022 B2
(45) Date of Patent: Jul. 1, 2025

(54) SYSTEMS AND METHODS FOR ULTRASONICALLY-ASSISTED PLACEMENT OF ORTHOPEDIC IMPLANTS

(71) Applicant: MiRus LLC, Marietta, GA (US)

(72) Inventors: Angad Singh, Marietta, GA (US); Jay Yadav, Sandy Springs, GA (US)

(73) Assignee: MiRus LLC, Marietta, GA (US)

( * ) Notice: Subject to any disclaimer, the term of this patent is extended or adjusted under 35 U.S.C. 154(b) by 72 days.

(21) Appl. No.: 18/229,421

(22) Filed: Aug. 2, 2023

(65) Prior Publication Data

US 2023/0397917 A1     Dec. 14, 2023

Related U.S. Application Data

(63) Continuation of application No. 16/884,977, filed on May 27, 2020, now Pat. No. 11,786,259.

(Continued)

(51) Int. Cl.
    *A61B 17/16*  (2006.01)
    *A61B 17/00*  (2006.01)
    (Continued)

(52) U.S. Cl.
    CPC .... *A61B 17/1655* (2013.01); *A61B 17/00234* (2013.01); *A61B 17/1604* (2013.01);
    (Continued)

(58) Field of Classification Search
    CPC . A61B 17/16; A61B 17/1613; A61B 17/1615; A61B 17/1617; A61B 17/1626;
    (Continued)

(56) References Cited

U.S. PATENT DOCUMENTS 5,255,669 A * 10/1993 Kubota .......... A61B 17/320068
                                                       601/3
6,204,592 B1   3/2001  Hur
                       (Continued)

OTHER PUBLICATIONS

Lian, X. et al., "Total 3D Airo Navigation for Minimally Invasive Transforaminal Lumbar Interbody Fusion". Biomed Research International, vol. 2016, pp. 1-8 (2016).

(Continued)

*Primary Examiner* — Eric S Gibson
(74) *Attorney, Agent, or Firm* — UB Greensfelder LLP; Brian E. Turung

(57) ABSTRACT

Systems and methods for ultrasonically-assisted placement of orthopedic implants is described herein. An example method may comprise delivering ultrasonic energy to a surgical instrument such as a screw driver, Jamshidi needle, awl, probe, or tap that is in contact with the bone region targeted for removal and/or being prepared for implant placement. The method may further comprise delivering the ultrasonic energy via a probe passed through a cannulated surgical instrument and/or implant. An example system may comprise an ultrasonic generator coupled to a transducer, a probe or surgical instrument coupled to the transducer, a cannulated surgical instrument that allows passage of the probe, and a computing device configured to control the ultrasonic generator and take input from the user.

28 Claims, 12 Drawing Sheets

Related U.S. Application Data

(60) Provisional application No. 62/853,255, filed on May 28, 2019.

(51) Int. Cl.
  *A61B 17/32* (2006.01)
  *A61B 17/70* (2006.01)
  *A61B 17/84* (2006.01)
  *A61B 17/86* (2006.01)
  *B06B 3/00* (2006.01)
  *A61B 17/34* (2006.01)

(52) U.S. Cl.
  CPC ...... *A61B 17/1615* (2013.01); *A61B 17/1626* (2013.01); *A61B 17/1628* (2013.01); *A61B 17/1631* (2013.01); *A61B 17/320068* (2013.01); *A61B 17/7001* (2013.01); *A61B 17/848* (2013.01); *A61B 17/864* (2013.01); *B06B 3/00* (2013.01); *A61B 2017/00106* (2013.01); *A61B 2017/00146* (2013.01); *A61B 2017/00292* (2013.01); *A61B 2017/00415* (2013.01); *A61B 2017/00973* (2013.01); *A61B 2017/3413* (2013.01)

(58) Field of Classification Search
  CPC ............ A61B 17/1628; A61B 17/1631; A61B 17/320068; A61B 2017/320069; A61B 2017/320071; A61B 2017/320072; A61B 2017/320073; A61B 2017/320082; A61B 2017/320084; A61B 2017/320088; A61B 2017/320089; A61B 2017/32009
  See application file for complete search history.

(56) References Cited

U.S. PATENT DOCUMENTS

| | | | | |
|---|---|---|---|---|
| 6,379,371 | B1 * | 4/2002 | Novak | A61B 17/320068 30/123.3 |
| 6,443,969 | B1 * | 9/2002 | Novak | A61B 17/320068 606/169 |
| 7,794,414 | B2 * | 9/2010 | Rabiner | A61B 17/22012 601/2 |
| 9,775,637 | B2 * | 10/2017 | Onuma | A61B 90/37 |
| 10,166,042 | B2 * | 1/2019 | Tanigami | A61B 17/3205 |
| 10,194,932 | B2 * | 2/2019 | Tanigami | A61B 17/320068 |
| 10,201,366 | B2 * | 2/2019 | Tanigami | A61B 17/320016 |
| 10,231,739 | B1 * | 3/2019 | Bonutti | A61B 17/155 |
| 10,265,549 | B2 * | 4/2019 | Tanigami | A61B 18/1402 |
| 10,314,661 | B2 * | 6/2019 | Bowling | A61B 34/32 |
| 10,321,921 | B2 * | 6/2019 | McGinley | A61B 17/1626 |
| 10,433,921 | B2 * | 10/2019 | Librot | A61B 34/10 |
| 10,588,645 | B1 * | 3/2020 | Cao | A61B 17/320068 |
| 10,687,841 | B2 * | 6/2020 | Murasawa | A61B 17/29 |
| 10,806,529 | B2 * | 10/2020 | Timperley | A61B 17/8808 |
| 10,973,610 | B2 * | 4/2021 | Halter | A61C 1/18 |
| 11,786,259 | B1 * | 10/2023 | Singh | A61B 17/1631 606/79 |
| 2008/0058845 | A1 * | 3/2008 | Shimizu | A61B 17/29 606/205 |
| 2008/0234709 | A1 * | 9/2008 | Houser | A61B 17/320068 606/169 |
| 2009/0163901 | A1 | 6/2009 | Fisher et al. | |
| 2009/0318945 | A1 | 12/2009 | Yoshimine et al. | |
| 2010/0121197 | A1 * | 5/2010 | Ota | A61B 17/320068 600/462 |
| 2012/0078278 | A1 * | 3/2012 | Bales, Jr. | A61B 17/320092 307/116 |
| 2012/0316474 | A1 * | 12/2012 | Bonutti | A61B 90/06 601/2 |
| 2013/0253387 | A1 * | 9/2013 | Bonutti | A61H 23/0245 601/46 |
| 2014/0135663 | A1 * | 5/2014 | Funakubo | A61B 17/320068 310/330 |
| 2015/0088137 | A1 * | 3/2015 | Manna | A61B 17/142 606/79 |
| 2015/0342618 | A1 * | 12/2015 | Nguyen | A61B 17/1688 433/27 |
| 2017/0035454 | A1 * | 2/2017 | Yoshimine | A61B 17/32002 |
| 2017/0086872 | A1 * | 3/2017 | Tanigami | A61B 17/320016 |
| 2017/0086874 | A1 * | 3/2017 | Tanigami | A61B 17/320016 |
| 2017/0086875 | A1 * | 3/2017 | Tanigami | A61B 17/320016 |
| 2017/0156737 | A1 * | 6/2017 | Tanigami | A61B 17/320068 |
| 2017/0165507 | A1 * | 6/2017 | Tanigami | A61B 18/1402 |
| 2017/0333052 | A1 | 11/2017 | Ding et al. | |
| 2017/0367727 | A1 * | 12/2017 | Sakai | A61B 17/320068 |
| 2018/0070975 | A1 * | 3/2018 | Onuma | A61B 17/1604 |
| 2018/0110572 | A1 * | 4/2018 | Flatt | A61B 34/30 |
| 2018/0116784 | A1 * | 5/2018 | Takayama | A61B 17/1675 |
| 2018/0185054 | A1 * | 7/2018 | Murasawa | A61B 17/32 |
| 2018/0289432 | A1 * | 10/2018 | Kostrzewski | A61B 34/20 |
| 2018/0353253 | A1 * | 12/2018 | Bowling | A61B 34/30 |
| 2019/0021752 | A1 * | 1/2019 | Boudreaux | A61B 17/320068 |
| 2019/0105073 | A1 * | 4/2019 | Tanigami | A61B 17/320068 |
| 2019/0201043 | A1 * | 7/2019 | Shelton, IV | A61B 18/1445 |
| 2019/0201075 | A1 * | 7/2019 | Shelton, IV | A61B 17/320068 |
| 2019/0231383 | A1 * | 8/2019 | Shimamura | G10K 11/02 |
| 2019/0239916 | A1 * | 8/2019 | Yoshimine | H04R 17/10 |
| 2019/0247058 | A1 * | 8/2019 | Fujisaki | A61B 17/320068 |
| 2019/0247077 | A1 * | 8/2019 | Fujisaki | A61B 17/1675 |
| 2019/0247080 | A1 * | 8/2019 | Yokoyama | A61B 17/16 |
| 2019/0262027 | A1 * | 8/2019 | Akagane | A61B 17/320068 |
| 2019/0274752 | A1 * | 9/2019 | Denzinger | A61B 17/320068 |
| 2019/0290317 | A1 * | 9/2019 | Onuma | A61B 18/1206 |
| 2019/0328458 | A1 * | 10/2019 | Shmayahu | A61B 5/064 |
| 2020/0093555 | A1 * | 3/2020 | Flatt | A61B 34/30 |
| 2020/0107848 | A1 * | 4/2020 | Apperson | A61B 17/32 |
| 2020/0113595 | A1 * | 4/2020 | Fujisaki | A61B 17/16 |
| 2020/0138469 | A1 * | 5/2020 | Fujisaki | A61B 17/16 |
| 2020/0138470 | A1 * | 5/2020 | Fujisaki | A61B 17/320068 |
| 2020/0138471 | A1 * | 5/2020 | Fujisaki | A61B 17/320068 |
| 2020/0146706 | A1 * | 5/2020 | Sawada | A61B 17/320068 |
| 2020/0222116 | A1 | 7/2020 | Yadav | |
| 2021/0093340 | A1 * | 4/2021 | Baker | A61B 17/22012 |
| 2021/0137612 | A1 * | 5/2021 | Staid | A61B 17/320016 |
| 2021/0212769 | A1 * | 7/2021 | Walen | A61B 17/15 |
| 2023/0397917 | A1 * | 12/2023 | Singh | A61B 17/7001 |

OTHER PUBLICATIONS

Shin, M-H et al., "Accuracy and Safety in Pedicle Screw Placement in the Thoracic and Lumbar Spines: Comparison Study between Conventional C-Arm Fluoroscopy and Navigation Coupled with O-Arm Guided Methods", J. Korean Neurosurg Soc, vol. 52, pp. 2004-2009 (2012).

* cited by examiner

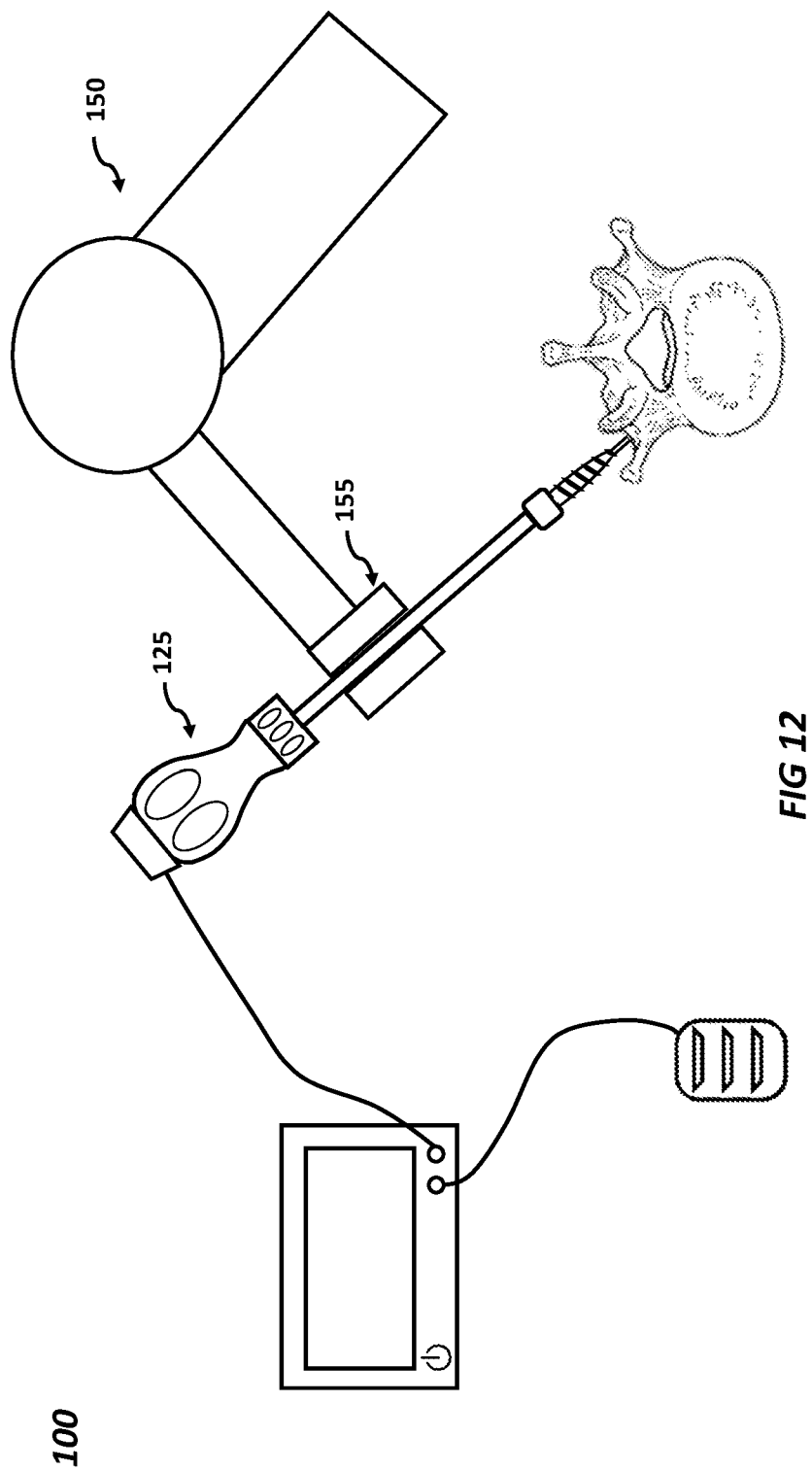

SYSTEMS AND METHODS FOR ULTRASONICALLY-ASSISTED PLACEMENT OF ORTHOPEDIC IMPLANTS

CROSS-REFERENCE TO RELATED APPLICATIONS

This application is a continuation of U.S. application Ser. No. 16/844,977 filed May 27, 2020, which in turn claims the benefit of U.S. provisional application No. 62/853,255, filed on May 28, 2019, and titled "SYSTEMS AND METHODS FOR ULTRASONICALLY-ASSISTED PLACEMENT OF ORTHOPEDIC IMPLANTS" the disclosure of which is expressly incorporated herein by reference in its entirety.

TECHNICAL FIELD

The present disclosure relates generally to orthopedic surgery and, more particularly, to a system and method for ultrasonically-assisted placement of orthopedic implants such as screws.

BACKGROUND

Many orthopedic surgeries, such as those involving the spine, are complex procedures that require a high degree of precision. For example, the spine is in close proximity to delicate anatomical structures such as the spinal cord and nerve roots. Placement of spinal implants such as pedicle screws are among the most effective schemes for stabilizing the spine. With pedicle diameters ranging from 4 to 20 mm, screw fixation into the pedicle requires great precision to avoid skiving, cortex violation, and/or damage to surrounding nerves and/or spinal cord. Compounding the problem is limited surgical exposure and visibility, particularly in the case of minimally invasive procedures. Consequently, the risk of misplaced implants or other complications is high.

Current means of implant site preparation and screw placement relies on rudimentary mechanical instrumentation such as sharp rigid instrumentation and rotary drills and burrs that impact high forces on the bone and increase the possibility of skiving or other inaccuracies due to bone movement such as in image guided surgeries. Consequently the screw placement lacks consistency and precision. Such uncertainty in screw placement has a negative impact on long term clinical outcomes, patient quality of life, and the ability to predict and control costs associated with surgery, recovery, and rehabilitation.

The presently disclosed systems and associated methods for ultrasonically-assisted placement of orthopedic implants are directed at overcoming one or more of the problems set forth above and/or other problems in the art.

SUMMARY

According to one aspect, the present disclosure is directed to a method for ultrasonically-assisted placement of implants such as screws. The method may comprise delivering ultrasonic energy to a surgical instrument such as a screw driver, Jamshidi needle, awl, probe, or tap that is in contact with the bone region targeted for removal and/or is being prepared for implant placement. The method may allow the user to use the mechanical abilities of the tool along with ultrasonic energy to accomplish the surgical goals. The method may also comprise delivering ultrasonic energy via a probe to the bone. The probe may be passed through a cannulated surgical instrument and/or implant. The probe is preferably in contact with the bone region targeted for removal. The method further comprises controlling the ultrasonic power, frequency, amplitude, pulse width, time, and other parameters such that removal rate and area of bone removal is tailored to the specific goals of the procedure. The method may further comprise switching between or combining rotary and ultrasonic vibratory modes of bone removal so as to achieve optimal placement of the implant. The method further comprises sensing and analyzing the reflected ultrasonic waves to determine properties of the material in contact with the probe or instruments and/or distances of objects, surfaces, and/or boundaries.

In accordance with another aspect, the present disclosure is directed to a tool for ultrasonic assisted placement of an implant. In one embodiment the tool is a cannulated surgical instrument such as a Jamshidi needle, awl, probe, or tap through which a probe is passed. This may allow the user to use the mechanical abilities of the tool along with ultrasonic energy to accomplish the surgical goals. In yet another embodiment the tool is a cannulated manual or powered screw driver coupled to a cannulated screw through which the probe is passed. This may also allow for ultrasonic energy to be utilized along with the normal functionality of a traditional manual or powered surgical screw driver. In yet another embodiment the handle of the tool is configured to accommodate at least a portion of the transducer.

In accordance with another aspect, the present disclosure is directed to a system for ultrasonic assisted placement of an orthopedic implant. The system comprises an ultrasonic generator coupled to a transducer and at least one computing device. The transducer may further be equipped with a horn comprising a tip configured to facilitate attachment to surgical instruments or to a probe. The probe may be used standalone or be passed through cannulated surgical instruments. The ultrasonic generator and/or the computing device is configured to control the ultrasonic power, amplitude of vibration, frequency, duration, pulses, and/or timing. The system is further configured to allow a user to interact with it for the purpose on controlling the ultrasonic energy by using I/O devices such as buttons, foot pedals, and/or touch screen display. The system may also consist of cannulated surgical instruments that accommodate the ultrasonic probe and allow utilization of ultrasonic vibratory energy in conjunction with conventional mechanical (e.g. rotary) modes to place the implant into the bony anatomy. The system may further be utilized in conjunction with image-guided navigation systems capable of real-time tracking of the instrument and/or implant position. The system may further consist of or be utilized with a robotically controlled arm and/or guide for precise positioning of the probe and/or surgical instrument.

BRIEF DESCRIPTION OF THE DRAWINGS

The components in the drawings are not necessarily to scale relative to each other. Like reference numerals designate corresponding parts throughout the several views.

FIG. 12 provides a diagrammatic view of another alternate exemplary system for ultrasonically-assisted placement of orthopedic implants consistent with certain disclosed embodiments.

DETAILED DESCRIPTION

Figure 1:
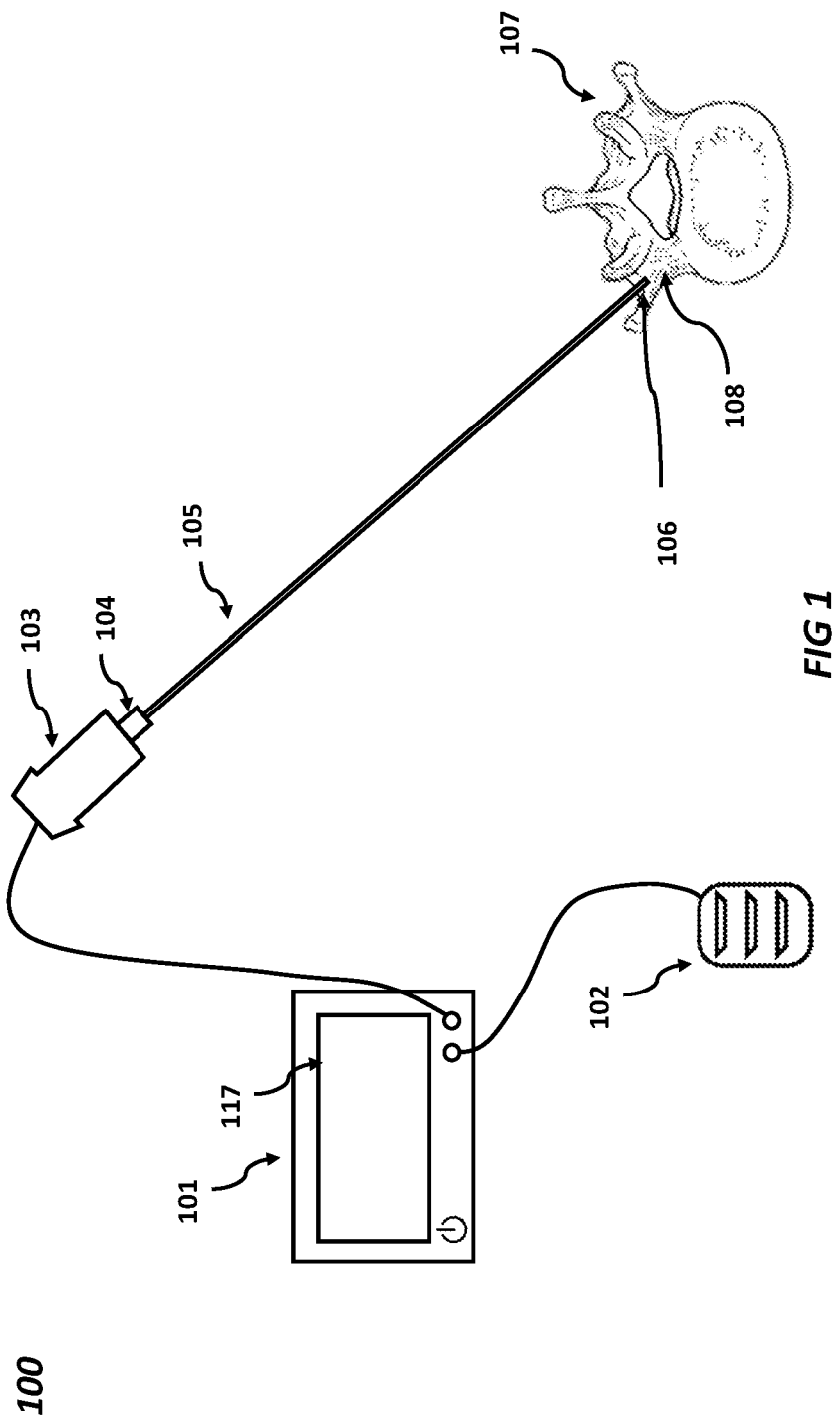
FIG. 1 provides a diagrammatic view of an exemplary system for ultrasonically-assisted placement of orthopedic implants consistent with certain disclosed embodiments.

FIG. 1 provides a diagrammatic view of exemplary system 100 for ultrasonically assisted placement of orthopedic implants. The system consists of a console 101 comprising at least one computing device (not shown) communicatively coupled to a touchscreen display 117, one or more 1/0 devices such as foot pedal 102, and an ultrasonic generator (not shown). The ultrasonic generator is electrically coupled to a transducer contained in handpiece 103 that may be coupled to a horn with a tip 104. A metallic flexible or rigid probe 105 with probe tip 106 is rigidly coupled to horn tip 104. The ultrasonic generator in console 101 produces electrical energy at ultrasonic frequencies that is then converted in mechanical vibrations by the transducer and horn in handpiece 103. These vibration are then further transmitted to probe tip 106 via the rigid coupling of probe 105 to horn tip 104. The transducer in handpiece 103 may also optionally serve as a sensor to sense reflected ultrasonic waves that can then be analyzed by algorithms implemented on the ultrasonic generator and/or computing device. Sensing and analysis of reflected waves can provide information regarding the properties of the material in contact with the probe or tool tip and or distances of surfaces, boundaries, and/or objects. Probe 105 delivers ultrasonic energy to its tip 106 which when in contact with the desired location on bone 107 will remove material and drill a hole. For example the ultrasonic energy delivered to the bone surface may be applied for a sufficient duration to remove sufficient material necessary to facilitate placement of an orthopedic screw (not shown) into pedicle 108 of vertebra 107. For e.g. the system 100 can be used to breach the cortex of vertebra 107 to open up an entry point into pedicle 108 for a pedicle screw.

Figure 2:
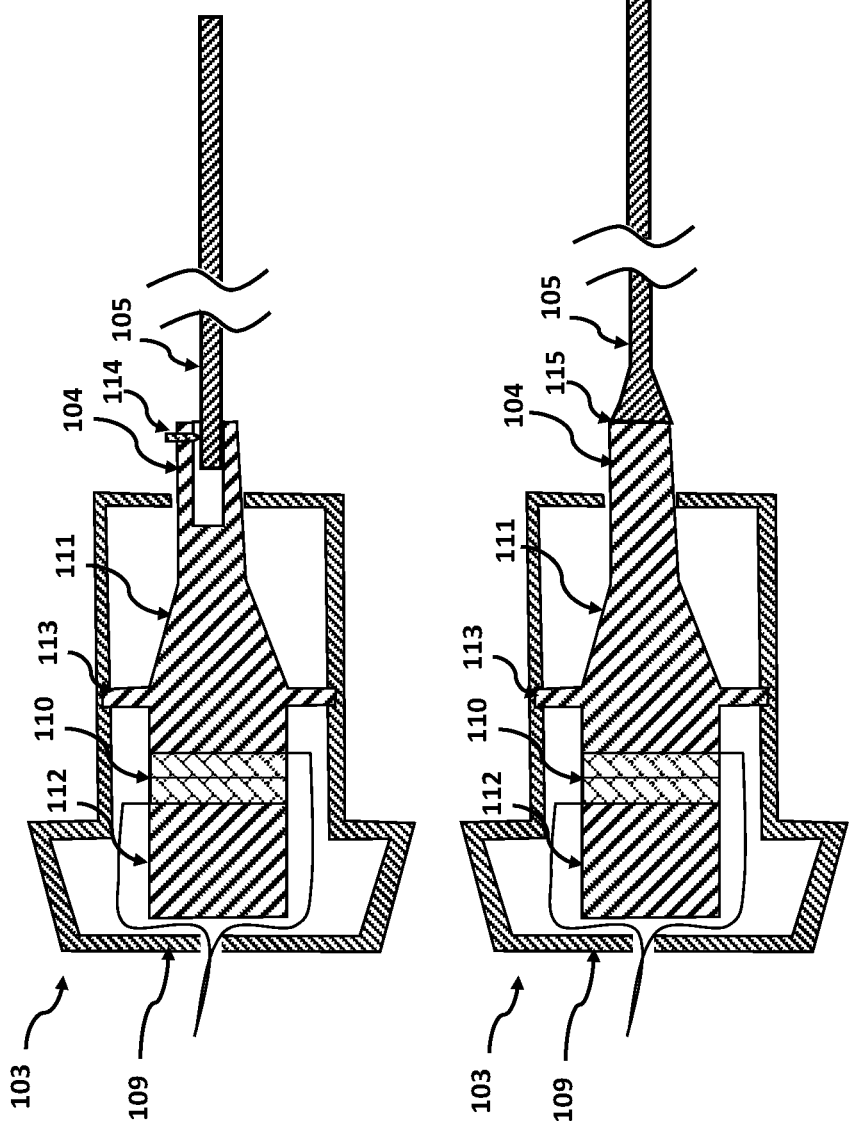
FIG. 2A provides a cross-sectional view of the handpiece and probe assembly of an exemplary system for ultrasonically-assisted placement of orthopedic implants consistent with certain disclosed embodiments.
FIG. 2B provides a cross sectional view of an alternate handpiece and probe assembly of an exemplary system for ultrasonically-assisted placement of orthopedic implants consistent with certain disclosed embodiments FIG. 3 provides a block diagram of an exemplary system for ultrasonically-assisted placement of orthopedic implants consistent with certain disclosed embodiments.

FIG. 2A is a cross section view of an exemplary assembly of hand piece 103 and probe 105. It comprises a housing 109 preferably made of an insulating material such as an insulating polymer. Example of a suitable insulating polymer is Delrin® from DuPont USA. Transducer may be a piezoelectric stack 110 comprising one or more layers sandwiched between an end cap 112 and horn 111. The horn may also have a one or more mounting flanges 113 to facilitate assembly in housing 109. The cap 112 and horn 111 are typically made of metal such as aluminum, titanium, or stainless steel alloys. The horn serves the purpose of increasing the amplitude of vibrations and facilitating transfer of vibrations to probe 105 coupled to the horn tip 104. The entire assembly comprising the transducer 110, end cap 112, horn 111, and probe 105 form an electro-mechanical system that is typically designed, simulated, and tuned to a desired resonant frequency to ensure optimal performance. Exemplary transducers and horn assemblies suitable for use in system 100 are piezoelectric horn transducers supplied by Beijing Ultrasonic, China. Probe 105 is a long wire that can be flexible but should be rigid/stiff enough for efficient energy transfer. Probe 105 is envisioned to have a length of 25-50 cm and diameter of 1-2 mm. Probe 105 can be made out of a suitable, and preferably biocompatible, metal alloy such a stainless steel 316L or titanium Ti-6Al-4V. The tip of the probe can be flat, sharp, trocar shaped, threaded or unthreaded depending on the application and material properties of the bone. The attachment of the probe 105 to horn tip 114 can be achieved using a variety of mechanical methods. One method, shown in FIG. 2A, is to use a set screw 114 that can tightened using an appropriate screw driver or Allen wrench. This method allows the probe 105 to slide in out of a hollow horn tip 104 thereby providing a means to adjust the length of probe extending out from the tip of the horn. Such length adjustability may be desirable in certain embodiments of system 100.

FIG. 2B shows a cross sectional view of an alternate exemplary assembly of handpiece 103 and probe 105. It is identical to FIG. 2A except for the method of attachment of probe 105 to horn tip 104. Instead of set screw, the attachment end of the probe 105 is terminated into a threaded cap that can screwed into horn tip 104. Such a connection may be more mechanically rigid and reliable that the set screw method.

Figure 3:
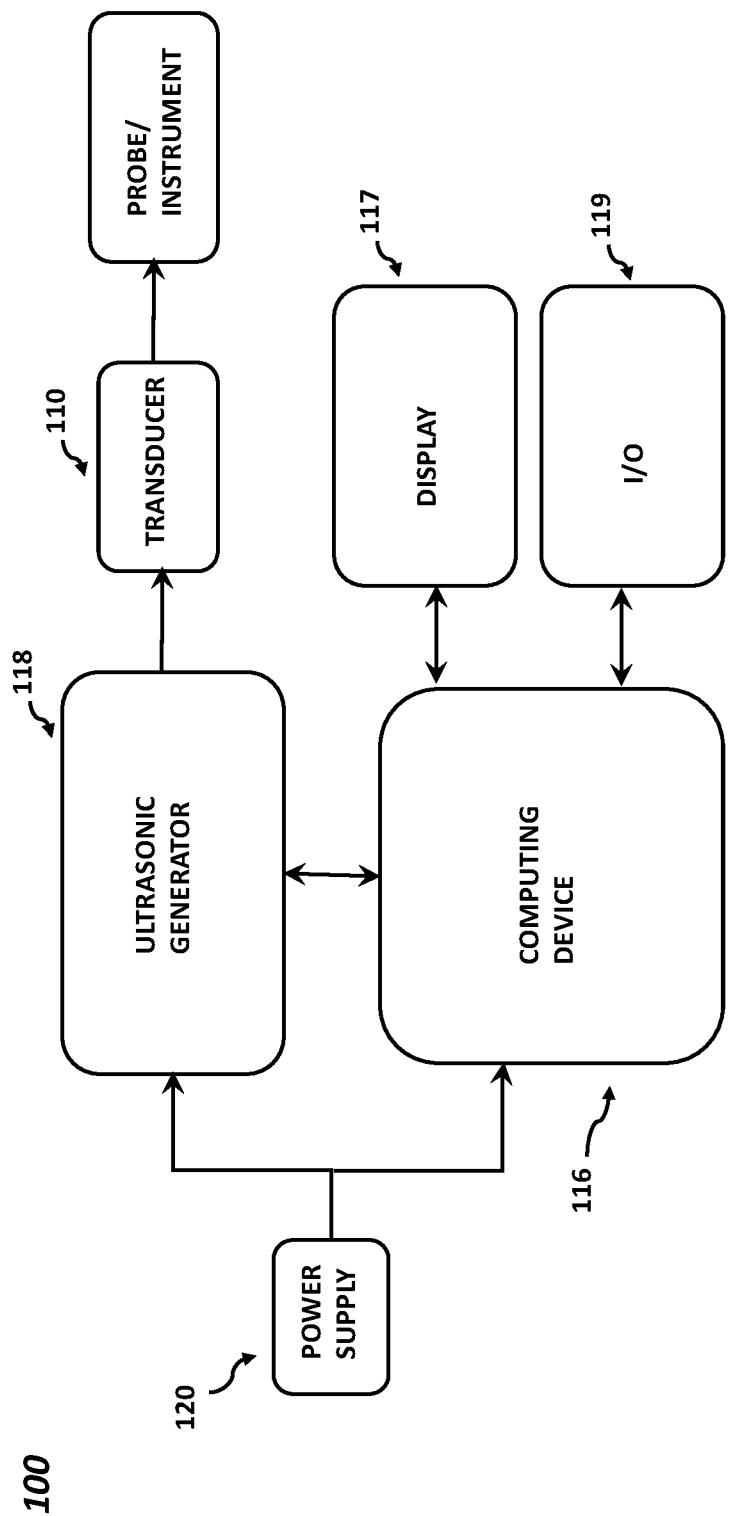

FIG. 3 shows a system block diagram of exemplary system 100. It comprises a computing device 116 communicatively coupled to an ultrasonic generator 118, display 117, and one or more I/O devices 119. Power supply 120 supplies power to all the electrical components above and can be an off-the-shelf medical grade power supply. It is envisioned that at least computing device 116, ultrasonic generator 118, and display 117 will be housed in a portable console that can be placed on table or cart (not shown). Computing device 116 can be any suitable embedded computing device such as a microcontroller, Single Board Computer (SBC) or Computer on Modules (COM). An example computing device suitable for use in system 100 is the Apalis COM module from Toradex, Seattle WA. The ultrasonic generator 118 can be any suitable ultrasonic generator that produces adequate power and range of frequencies for drilling of bone. It may also be equipped with algorithms and/or circuitry for resonant frequency, power, and impedance tracking. It is expected that the ultrasonic generator will produce between 20 W and 200 W of power at frequencies of 10 to 150 KHz which can be further narrowed depending on the specifics of the application. The ultrasonic generator 118 is electrically coupled to transducer 110 which is coupled to a probe as previously described. An exemplary ultrasonic generator 118 that can used in system 100 are ultrasonic generators produced by PiezoDrive, Australia. Display 117 can be any resistive or capacitive touch screen display compatible with the computing device 116. I/O devices 119 preferably includes at least a foot pedal (102 in FIG. 1) and may include one or more push buttons on console 101 in addition to touch screen inputs via display 117. For example, foot pedal 102 may be utilized to turn ON/OFF the vibrations and provide the user hands-free control of the application of vibratory energy.

Although the system shown in FIG. 1 can be used as a stand-alone system to drill bone via contact of the probe with the bone surface, its typical use is expected to be in combination with various cannulated surgical instruments and/or implants. In such embodiments, the length of probe 105 is selected such that it can be passed through the cannula of the instruments and/or implants with its tip 106 extending out from the instrument or implant end ready for contact with the bone surface. It is expected that system 100 will be configured such that the probe tip 106 will extend out between 2 to 20 mm from the instrument or implant end. To accommodate the probe, the cannula of the surgical instrument and/or implant should be larger than the probe diameter and it is expected to be in the range of 1-3 mm.

Figure 4:
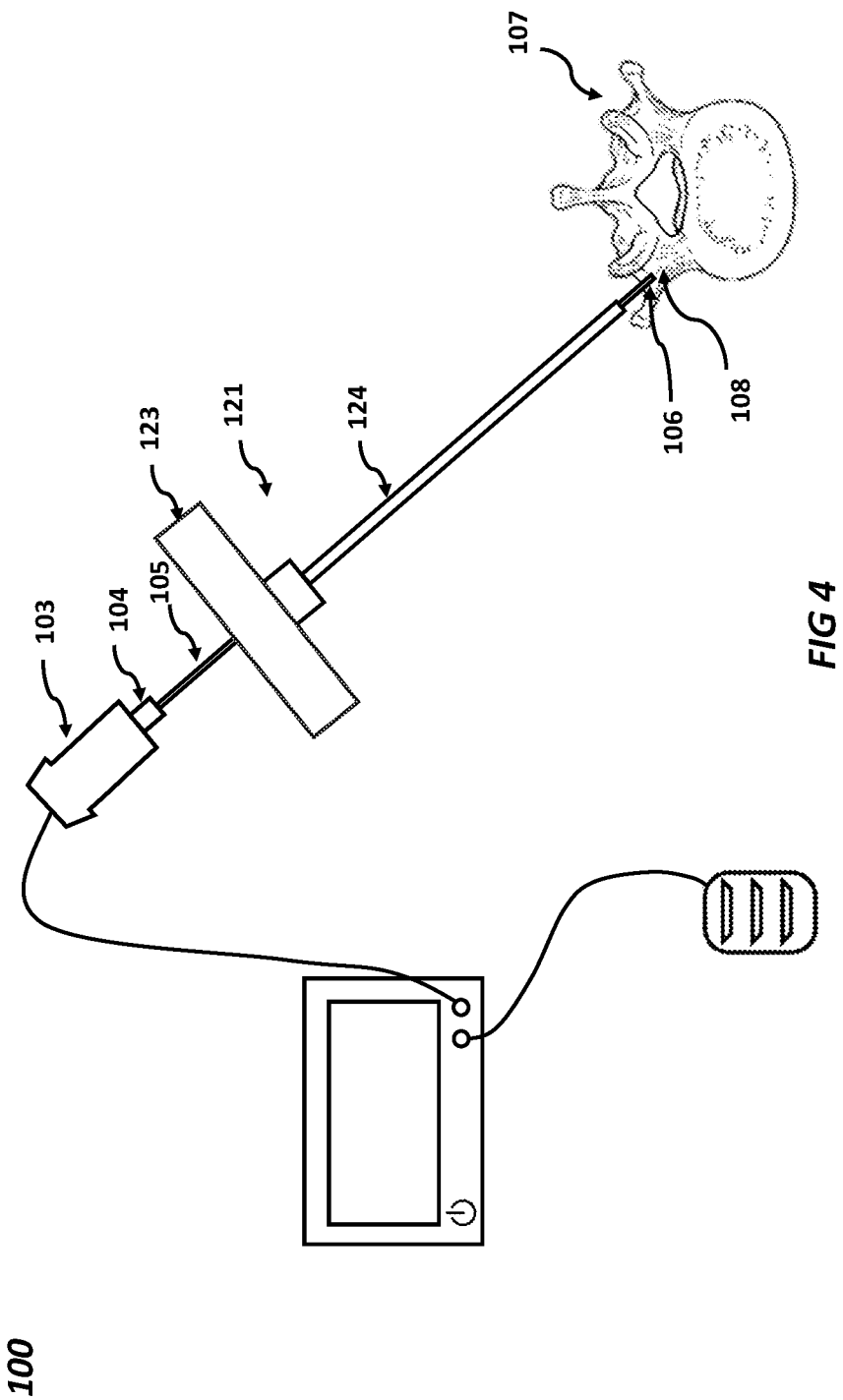
FIG. 4 provides a diagrammatic view of an alternate exemplary system for ultrasonically-assisted placement of orthopedic implants consistent with certain disclosed embodiments.

FIG. 4 provides a diagrammatic view of one such exemplary system 100. In this embodiment, probe 105 is passed through a cannulated surgical instrument 121 and delivers ultrasonic energy to the bone 107 at location 108. Examples of cannulated surgical instruments are Jamshidi needle, awls, probes, and/or taps. Such instruments may comprise a cannulated handle 123 and shaft 124. The system 100 may allow the user to combine rotary and other conventional mechanical modes of operation of instrument 121 with ultrasonic vibratory energy transmitted via probe tip 106 to remove bone at a desired location and/or to a desired depth. For example, the surgical instrument 121 may be rotated or mechanically interact with bone 107 while ultrasonic energy is being transmitted either concurrently or intermittently, to breach the cortex of vertebra 107 to prepare a pilot hole for placement of a pedicle screw into pedicle 108. The use of ultrasonic energy is expected to facilitate such pilot hole preparation with reduced forces and eliminate the need for high-speed rotary power tools.

Figure 5:
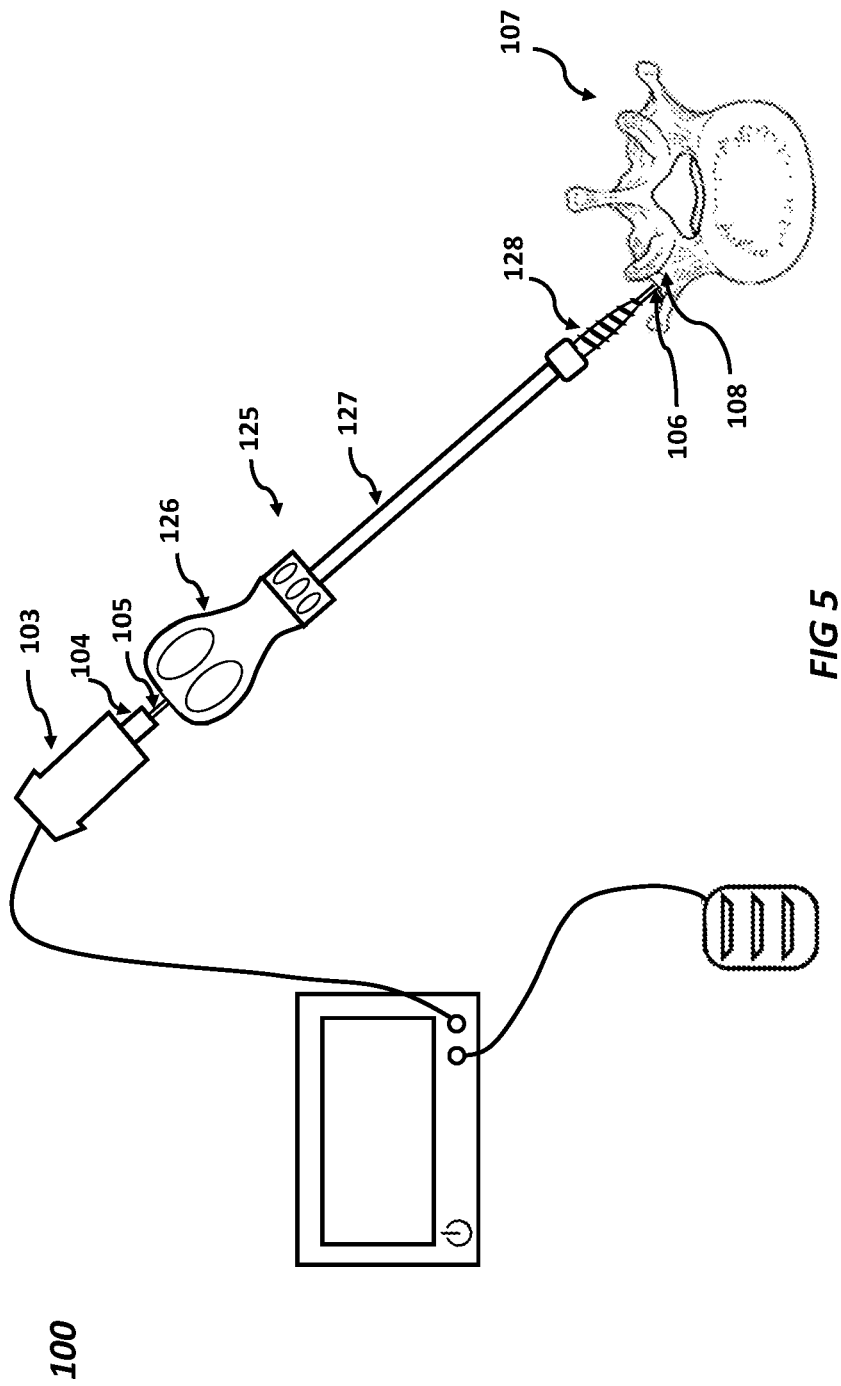
FIG. 5 provides a diagrammatic view of another alternate exemplary system for ultrasonically-assisted placement of orthopedic implants consistent with certain disclosed embodiments.

FIG. 5 provides a diagrammatic view of another alternate exemplary system for ultrasonically-assisted placement of orthopedic implants consistent with certain disclosed embodiments. In this embodiment the probe 105 is passed through a cannulated screw driver 125 which may comprise a cannulated handle 126 and shaft 127. A cannulated screw 128 may be loaded onto the shaft 127. As is the case with the surgical instrument, the screw cannula diameter should be larger than the probe and is expected to be in the range of 1-3 mm. The probe 105 is passed all the way through the handle 126, drive shaft 127 and screw 128 and until its tip 106 extends between 2-mm from the screw tip. The extent of the tip's extension may be controlled and adjusted based on clinician preferences and the surgical task at hand and the system 100 is expected to provide at least some adjustability of the tip extension for a given probe length. The probe in the configuration as described above delivers ultrasonic energy to the bone 107 at location 108. The surgical instrument 130 may combine rotary or other conventional modes of uses with ultrasonic energy to remove bone and drive the screw at the desired location and/or to the desired depth. For example, the screw 128 may be rotated/torqued and tip 106 ultrasonically vibrated at the same time or intermittently to breach cortex of vertebra 107 and place pedicle screw 128 into pedicle 108. Such a combination of ultrasonic vibratory energy with the conventional action of a screw driver is expected to facilitate screw placement with reduced forces and improved accuracy and greatly simplify the work flow and instrumentation.

Figure 6:
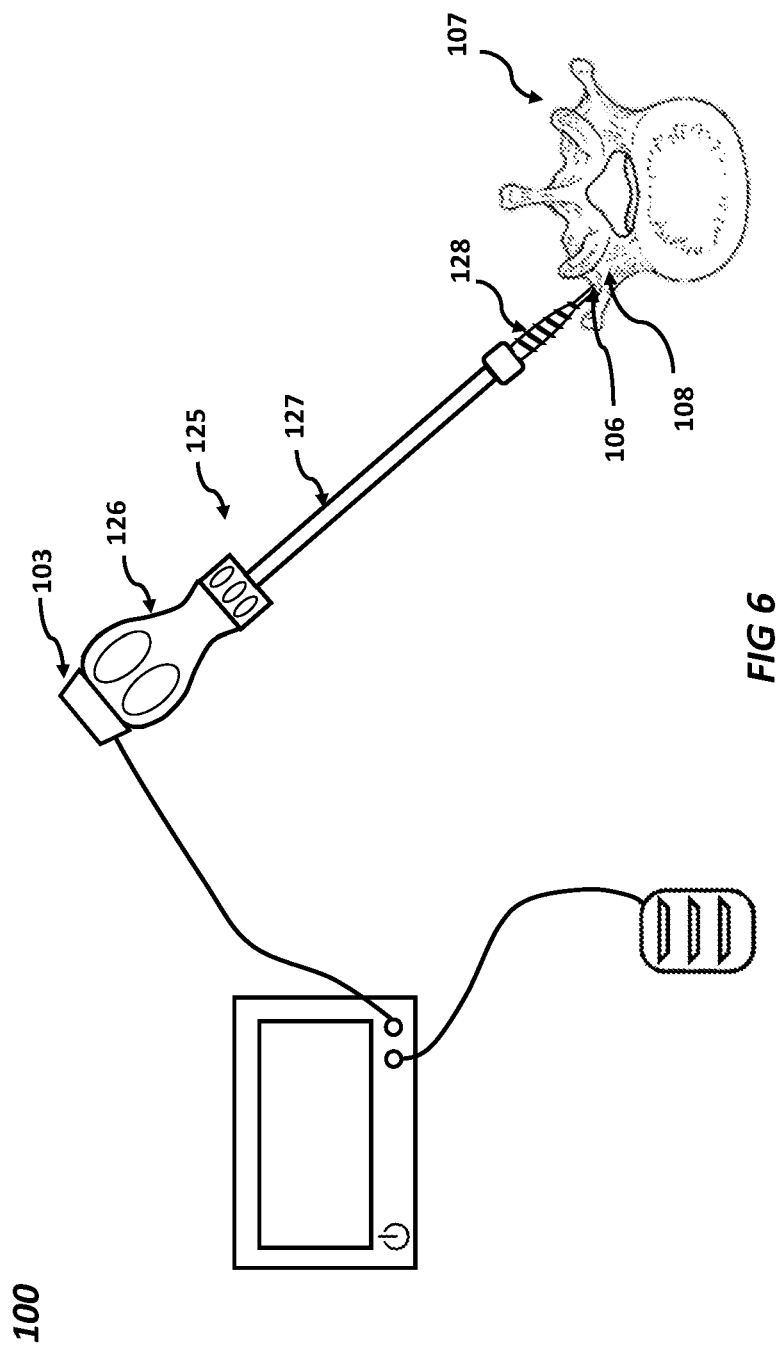
FIG. 6 provides a diagrammatic view of another alternate exemplary system for ultrasonically-assisted placement of orthopedic implants consistent with certain disclosed embodiments.

FIG. 6 provides a diagrammatic view of another alternate exemplary system for ultrasonically-assisted placement of orthopedic implants consistent with certain disclosed embodiments. The system is identical to the one above (FIG. 5) except that at least a portion of hand piece 103, and preferably a substantial portion of it, is housed inside the handle 126 of screw driver 125. This is expected to significantly improve the ergonomics and/or ease of use of the system.

Figure 7:
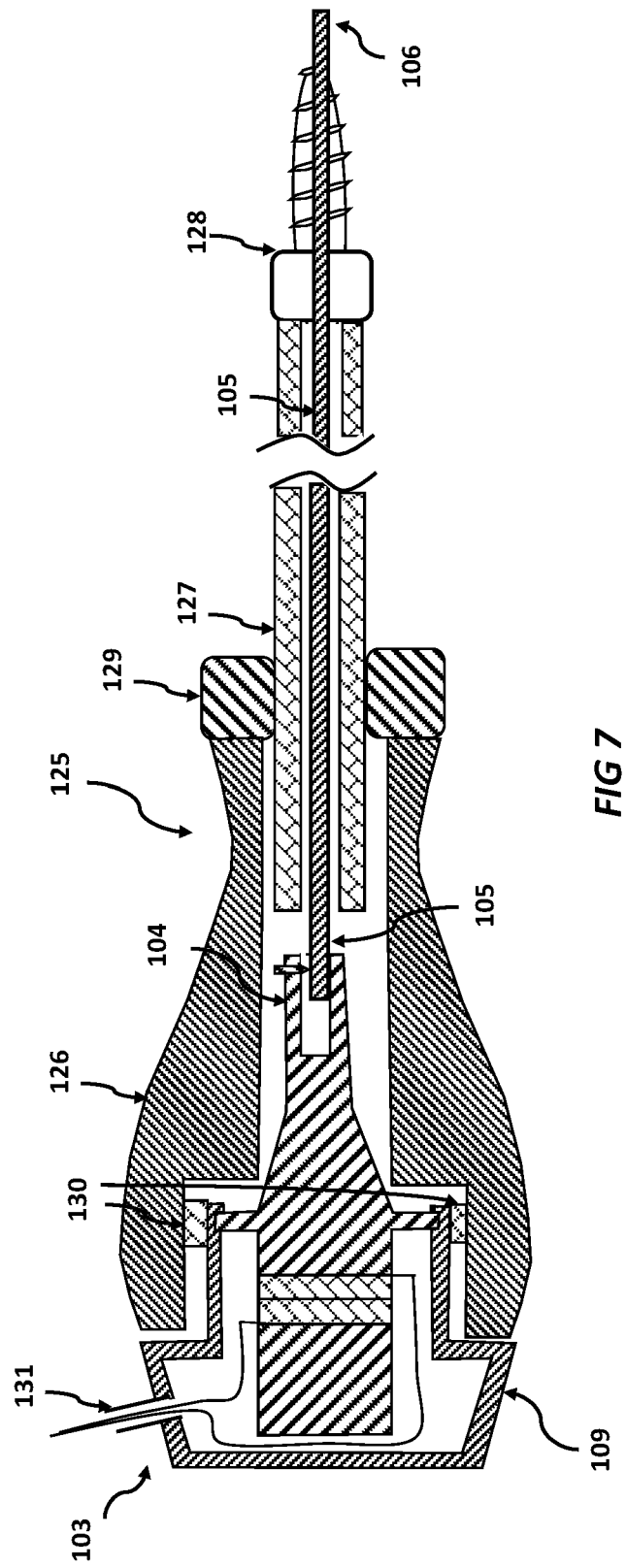
FIG. 7 provides a cross-sectional view of the hand-piece, screw driver, and probe assembly for the above alternate exemplary system for ultrasonically-assisted placement of orthopedic implants consistent with certain disclosed embodiments.

FIG. 7 is a cross-sectional of view of the handpiece 103 and screw driver 125 assembly for the alternate exemplary system 100 in FIG. 6. Handpiece 103 has an internal configuration and connection of horn tip 104 to probe 105 similar to the configuration in FIG. 2A as previously described. However in this embodiment the handle 126 of screw driver 125 is recessed to create room to accommodate a substantial portion of hand piece 103. Electrical connections to the transducer exit from a side port 131 to leave room on the top surface which may facilitate use of a 'palm grip' to grab the top of the handle 126 with minimal interference from handpiece 103. The mechanical attachment of handpiece 103 to handle 126 is via a bearing or low friction sliding contact 130 that allows easy relative rotation between the handle 126 and hand piece 103. This may facilitate torqueing/rotation of the screw driver without causing rotation of the handpiece 103 and any electrical cabling attached to it. Handle 126 may also comprise a ratcheting mechanism 129 for torque direction control and ease of use.

Figure 8:
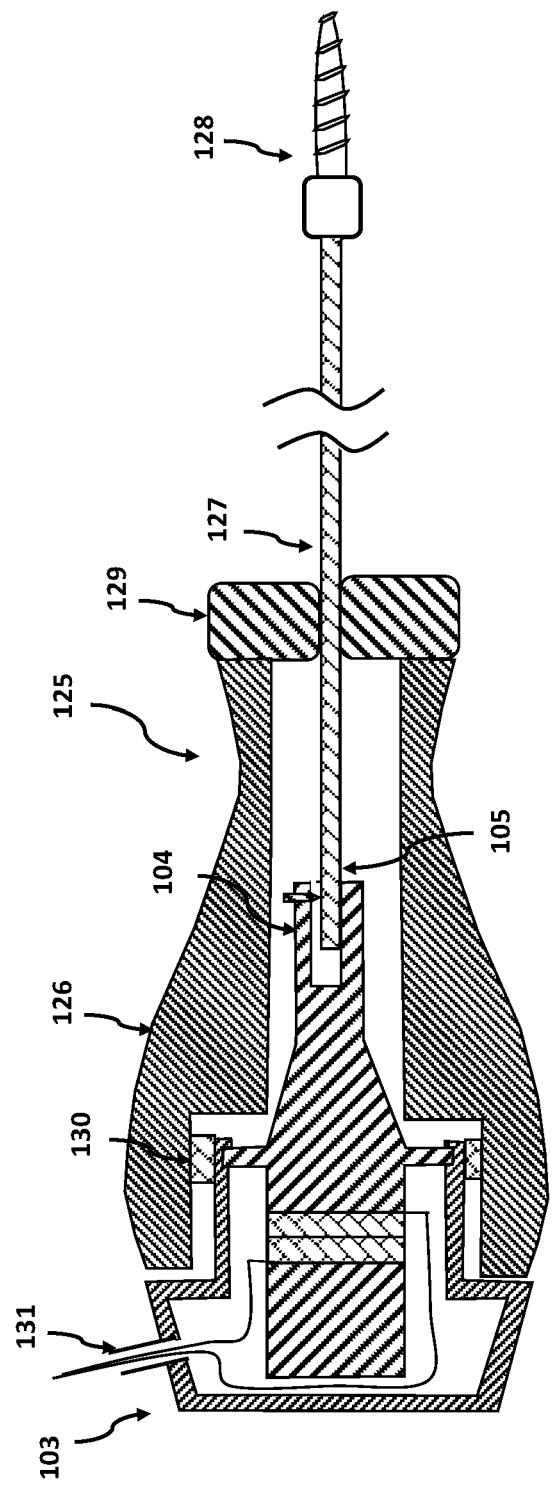
FIG. 8 provides a cross-sectional view of the hand-piece and screw driver assembly for an alternate exemplary system for ultrasonically-assisted placement of an orthopedic implant consistent with certain disclosed embodiments.

FIG. 8. is a cross-sectional of view of the handpiece 103 and screw driver 125 assembly for an alternate exemplary system 100. Instead of a using a probe as shown in FIG. 7, the horn tip 104 is directly coupled to shaft 127 of screw driver 125 such that the shaft 127 itself transmits ultrasonic energy to the tip of screw 128. The shaft 127 and screw 128 do not need to be cannulated in this embodiment. It is envisioned that such a configuration would be suited to small sized screws and associated instrumentation such as those utilized for cervical spine procedures.

Figure 9:
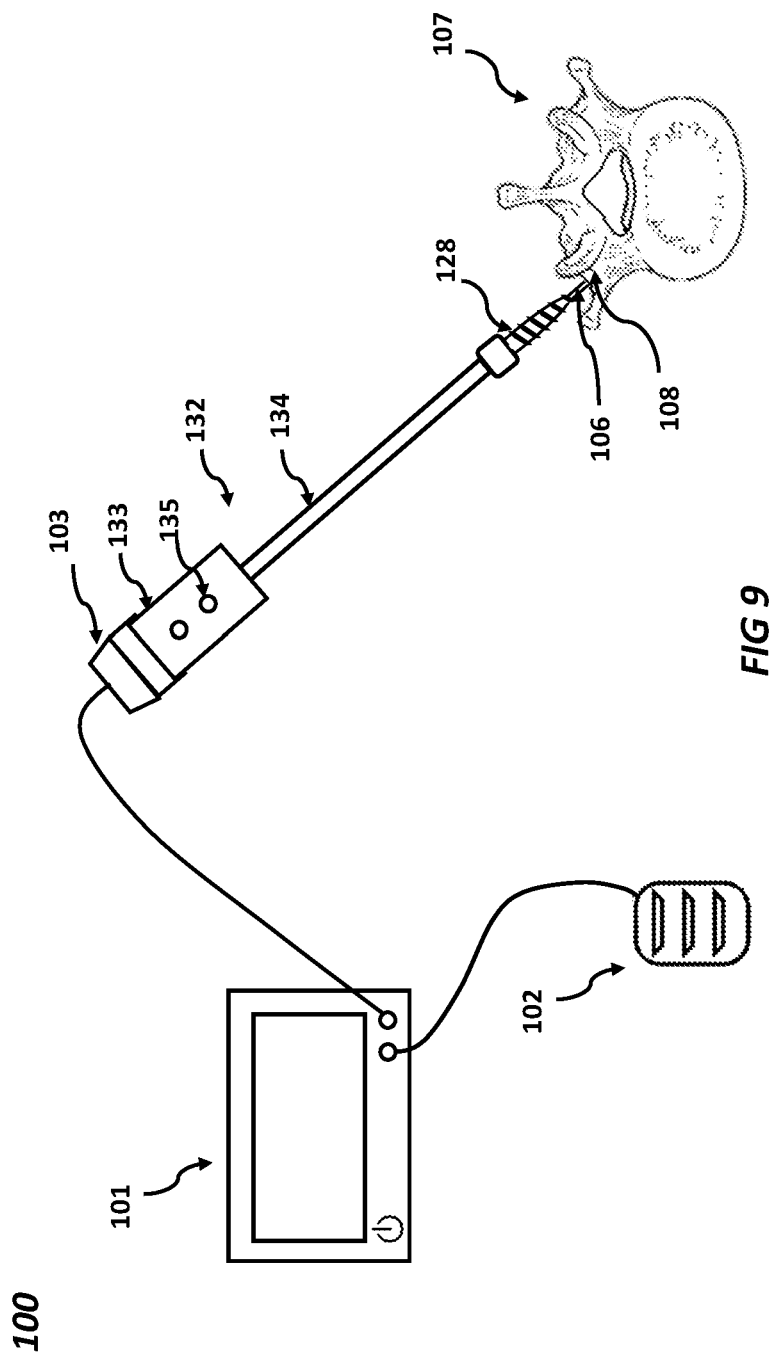
FIG. 9 provides a diagrammatic view of another alternate exemplary system for ultrasonically-assisted placement of orthopedic implants consistent with certain disclosed embodiments.

FIG. 9 provides a diagrammatic view of another alternate exemplary system for ultrasonically-assisted placement of orthopedic implants consistent with certain disclosed embodiments. Like the systems in FIGS. 5 and 6, the purpose of the system is to facilitate driving of screw 128 using ultrasonic vibratory energy coupled to probe tip 106. However, instead of a manual screw driver, this embodiment utilizes a power driver 132 that comprises a cannulated handle 133 and shaft 134. The power driver handle 133 may also comprise one or more buttons 135 to control the operation of the driver. This embodiment of the system 100 further reduces the amount of force needed to be imparted by the user to drive the screw 128 into pedicle 108 of vertebra 107.

Figure 10:
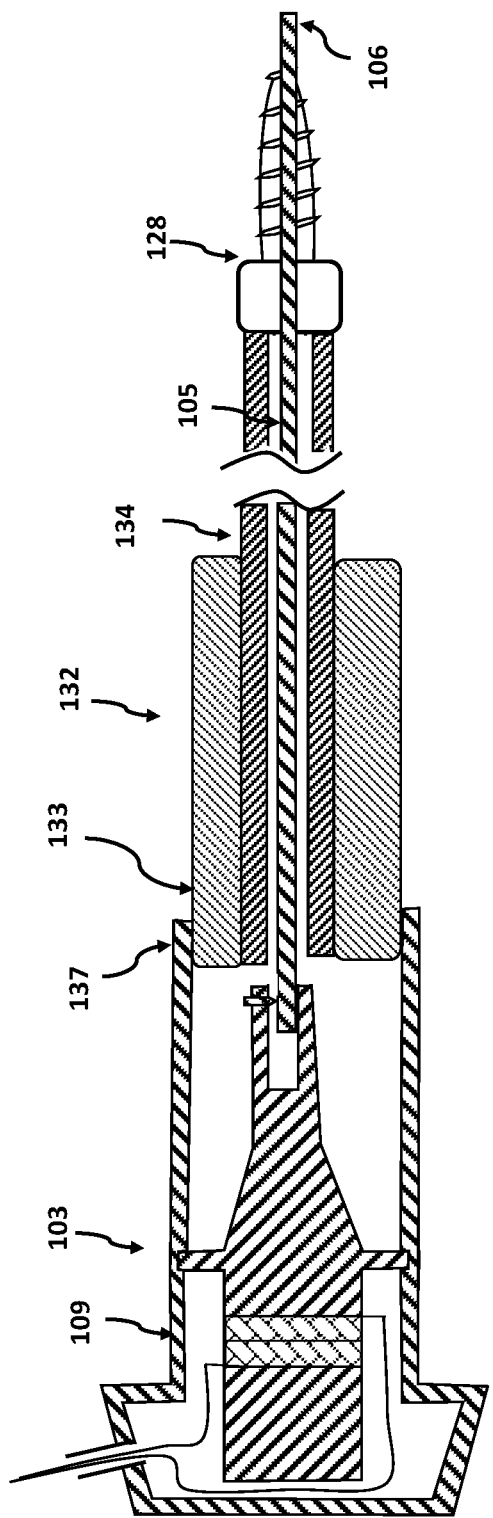
FIG. 10 provides a cross-sectional view of the hand-piece, screw driver, and probe assembly for the above alternate exemplary system for ultrasonically-assisted placement of orthopedic implants consistent with certain disclosed embodiments.

FIG. 10 is a cross-section of view of the handpiece 103 and screw driver 132 assembly for the alternate exemplary system 100 of FIG. 9. The handle 133 that comprises the motor (not shown) and shaft 134 assembly is also provisioned with a means to attach to housing 109 of handpiece 103. For example the attachment could be threaded connection 137 which not only ensures rigidity but also adjustability of the distance the probe tip 106 extends from the tip of screw 128.

Figure 11:
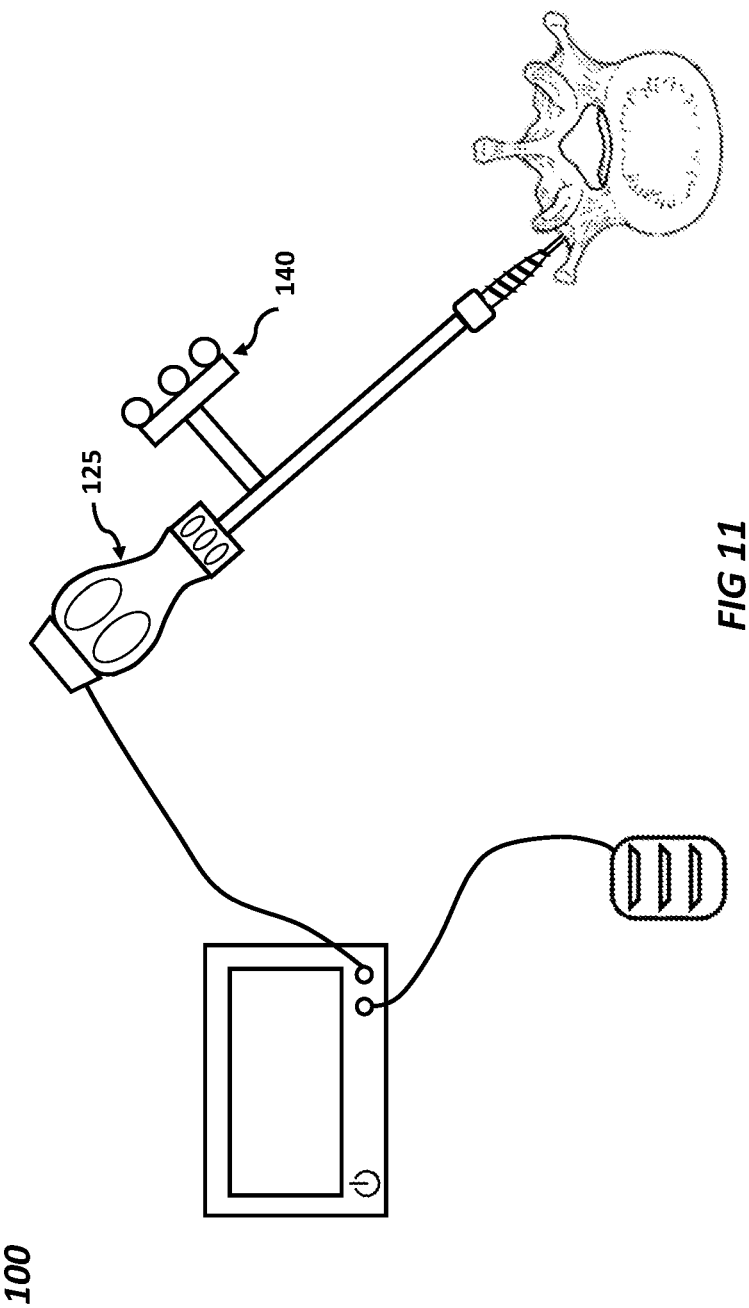
FIG. 11 provides a diagrammatic view of another alternate exemplary system for ultrasonically-assisted placement of orthopedic implants consistent with certain disclosed embodiments.

FIG. 11 provides a diagrammatic view of another alternate exemplary system for ultrasonically-assisted placement of orthopedic implants consistent with certain disclosed embodiments. In this embodiment, the instrument 125 is navigated using a surgical navigation system. Example surgical navigation system suitable for use with system 100 is the StealthStation system from Medtronic, Ireland. Such systems may rely on infra-red optical tracking and require the instrument to be rigidly attached to an array of infra-red reflector balls 140. The navigation system may be used in conjunction with any of the systems described above (FIGS. 1, 4, 5, 6, 8, 9).

FIG. 12 provides a diagrammatic view of another alternate exemplary system for ultrasonically-assisted placement of orthopedic implants consistent with certain disclosed embodiments. In this system robotic arm 150 is used to position the instrument 125 and may optionally use a guide 155 attached to the end of the robotic arm. Example robotic system suitable for use with system 100 is the Mazor-X robotic system from Medtronic, Ireland. The robotic arm may be used in conjunction with any of the systems described above (FIGS. 1, 4, 5, 6, 8, 9).

It will be apparent to those skilled in the art that various modifications and variations can be made to the disclosed systems and methods for ultrasonically-assisted placement of an orthopedic implant. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents

What is claimed is:

1. A method for ultrasonically-assisted placement of an orthopedic implant comprising:
   providing a surgical instrument; said surgical instrument includes a bone removal tip portion;
   providing an ultrasonic probe; said ultrasonic probe incudes a probe tip; at least a portion of said ultrasonic probe positioned in a cavity of said bone removal tip portion;
   providing an ultrasonic energy system that is connected to said ultrasonic probe;
   positioning said surgical instrument at or near a bone surface in a patient such that said bone removal tip portion is positioned at or near said bone surface;
   positioning said ultrasonic probe toward said bone surface until said probe tip is positioned at or near said bone surface; and,
   delivering ultrasonic energy from said ultrasonic energy system to said ultrasonic probe in sufficient ultrasonic power and/or duration to cause removal of bone on said bone surface at or near said probe tip.

2. The method as defined in claim 1, wherein said surgical instrument is a cannulated surgical instrument; and further including the step of at least partially inserting said ultrasonic probe into a cannula of said surgical instrument during said step of moving said ultrasonic probe toward said bone surface.

3. The method as defined in claim 2, wherein the surgical instrument is selected from the group consisting of a a tap, and a screw driver.

4. The method as defined in claim 3, further including the step of sensing and analyzing reflected ultrasonic waves from said bone surface to a) determine material properties of said bone, b) determine distances of said probe tip from relative to said bone and/or an object about said bone.

5. The method as defined in claim 4, further including the step of controlling said ultrasonic power, said duration, an amplitude of an ultrasonic wave, and/or a frequency of an ultrasonic wave to said probe tip.

6. The method as defined in claim 5, further including the step of a) simultaneously removing material from said bone surface using said ultrasonic probe and rotating said surgical instrument, and/or b) removing material from said bone surface by alternating use of said ultrasonic probe and rotation of said surgical instrument.

7. The method as defined in claim 1, wherein the surgical instrument is selected from the group consisting of a a tap, and a screw driver.

8. The method as defined in claim 1, further including the step of sensing and analyzing reflected ultrasonic waves from said bone surface to a) determine material properties of said bone, b) determine distances of said probe tip from relative to said bone and/or an object about said bone.

9. The method as defined in claim 1, further including the step of controlling said ultrasonic power, said duration, an amplitude of an ultrasonic wave, and/or a frequency of an ultrasonic wave to said probe tip.

10. The method as defined in claim 1, further including the step of a) simultaneously removing material from said bone surface using said ultrasonic probe and rotating said surgical instrument, and/or b) removing material from said bone surface by alternating use of said ultrasonic probe and rotation of said surgical instrument.

11. The method as defined in claim 1, wherein said ultrasonic probe is at least partially a flexible probe.

12. The method as defined in claim 1, wherein said ultrasonic probe is a rigid probe.

13. The method as defined in claim 1, wherein said ultrasonic probe is attached to a robotic arm.

14. The method as defined in claim 13, wherein said ultrasonic probe is at least partially positioned in a screwdriver.

15. The method as defined in claim 14, wherein said probe tip extends beyond a threaded end portion of said screwdriver.

16. The method as defined in claim 1, wherein said ultrasonic probe is movable along a longitudinal length of said surgical instrument.

17. The method as defined in claim 1, wherein said ultrasonic probe is fixed in positioned relative to a longitudinal length of said surgical instrument.

18. A system for ultrasonically-assisted placement of an orthopedic implant comprising:
   a surgical instrument; said surgical instrument includes a bone removal tip portion;
   an ultrasonic probe; said ultrasonic probe incudes a probe tip; at least a portion of said ultrasonic probe positioned in a cavity of said bone removal tip portion;
   an ultrasonic energy system that is connected to said ultrasonic probe; and wherein said ultrasonic energy system is configured to provide ultrasonic power to said probe tip.

19. The system as defined in claim 18, wherein said surgical instrument is a cannulated surgical instrument; and wherein at least a portion of said ultrasonic probe is located in a cannula of said surgical instrument.

20. The system as defined in claim 19, wherein the surgical instrument is selected from the group consisting of a tap, and a screw driver.

21. The system as defined in claim 20, wherein said ultrasonic energy system is configured to a) determine material properties of said bone based at least partially on reflected ultrasonic waves from a bone surface, b) determine distances of said probe tip from relative to a bone and/or object about the bone based at least partially on reflected ultrasonic waves from a bone surface.

22. The system as defined in claim 18, wherein the surgical instrument is selected from the group consisting of a tap, and a screw driver.

23. The system as defined in claim 18, wherein said ultrasonic energy system is configured to a) determine material properties of said bone based at least partially on reflected ultrasonic waves from a bone surface, b) determine distances of said probe tip from relative to a bone and/or object about the bone based at least partially on reflected ultrasonic waves from a bone surface.

24. The system as defined in claim 18, wherein said ultrasonic probe is at least partially a flexible probe.

25. The system as defined in claim 18, wherein said ultrasonic probe is a rigid probe.

26. The system as defined in claim 18, wherein said ultrasonic probe is attached to a robotic arm.

27. The system as defined in claim 18, wherein said ultrasonic probe is at least partially positioned in a screwdriver.

28. The system as defined in claim 27, wherein said probe tip extends beyond a threaded end portion of said screwdriver.

* * * * *